United States Patent [19]

Sarui

[11] 4,331,137
[45] May 25, 1982

[54] APPARATUS FOR TREATING ATHLETE'S FOOT

[76] Inventor: Kiichiro Sarui, 26-15 Takadanobaba 4-chome, Shinjuku-ku, Tokyo, Japan

[21] Appl. No.: 188,602

[22] Filed: Sep. 18, 1980

[30] Foreign Application Priority Data

Jul. 22, 1980 [JP] Japan .................................. 55-99343

[51] Int. Cl.³ ............................................ A61M 11/00
[52] U.S. Cl. ............................. 128/200.16; 128/256; 128/368; 128/402
[58] Field of Search ................... 128/200.16, 256, 368, 128/402, 207.19, 207.21, 260

[56] References Cited

U.S. PATENT DOCUMENTS

| | | | |
|---|---|---|---|
| 1,110,494 | 9/1914 | Kellogg | 128/402 |
| 1,399,095 | 12/1921 | Webb, Sr. | 128/402 |
| 2,825,336 | 3/1958 | Svoboda | 128/368 |
| 3,101,716 | 8/1963 | Cornell, Jr. | 128/402 |
| 3,565,072 | 2/1971 | Gauthier | 128/200.16 |

Primary Examiner—Henry J. Recla
Attorney, Agent, or Firm—Wenderoth, Lind & Ponack

[57] ABSTRACT

An apparatus for treating athlete's foot includes an inner box placed in an outer box, and having a space between the internal walls of the outer box and the external walls of the inner box. The interior of the inner box serves as an aerosol chamber. A heat source is provided in the lower part of the aerosol chamber, and an aerosol generating plate is placed thereon. An ultrasonic-wave oscillator, directed toward the interior of the aerosol chamber, is attached to the ceiling of the aerosol chamber. An exhaust port communicating with the interior of the outer box is provided in the upper part of the aerosol chamber. An exhaust filter and an exhaust fan are provided in the upper part of the outer box. A common opening through which the part affected with athlete's foot is to be inserted is provided in one side of both the outer and inner boxes. The common opening is closed with a sealing member. The space between the outer and inner boxes prevents the heat generated within the inner box from being transmitted outside. The exhaust fan and filter attached to the outer box absorb, filter, and expel the aerosol generated in the inner box, preventing the smell of the aerosol from leaking outside.

1 Claim, 3 Drawing Figures

APPARATUS FOR TREATING ATHLETE'S FOOT

BACKGROUND OF THE INVENTION

Athlete's foot is a common name for pompholyx ringworm, a kind of skin disease which forms on soles, palms and interdigital surfaces of hands and feet, and is caused by a kind of filamentous fungus classed as trichophyton. Favus producing white round desquamating macula and ringworm also fall into the same classification which is often called dartre or herpes. In Japan, for example, athlete's foot spreads in the rainy season and in the summer. Various kinds of medicines thus far proposed have been unable to cure this disease completely. Therefore, the disease remains uncured over the winter, and then begins to spread again from around April or May of the following year. Athlete's foot the world over exhibits more or less the same tendency.

The inventor has previously discovered that an aerosol of the oxide of some oils have a high curative effect on athlete's foot. When oxidized by light, heat and/or catalyst, a vegetable oil consisting mainly of glycerides of linolic, cleic, palmitic, stearic, arachidinic and other similar acids forms a peroxide, which then decomposes to generate a gaseous body known as an aerosol. This aerosol consists mainly of alcohol, aldehyde, ketone, lactonic oxides, glycolic, valeric and acetic acids plus other complex components. On contacting the athlete's foot-affected part, this aerosol reacts to turn the lesion into a humid powdery starch-like crust or, when having reached a greater depth, into a white cotton-waste-like crust, comprising 3 to 8 mm long fibers, which desquamates like a spider's threads, although some variations are seen depending upon the nature of the fungus. By repeating this treatment until the above-described condition is reached, athlete's foot can be cured completely.

The inventor invented an apparatus for treating athlete's foot as described in the Japanese Utility Model No. 55-5156. This apparatus comprises an aerosol chamber which contains a plate to carry an aerosol generating substance and a heat source and has a window to insert the affected zone on hand or foot. This apparatus, however, has not been without some shortcomings, such as the leaking of the ill-smelling aerosol and the heating of the exterior walls of the apparatus.

SUMMARY OF THE INVENTION

An bject of this invention is to provide an apparatus for treating athlete's foot which does not emit an effensive smell.

Another object of this invention is to provide an apparatus for treating athlete's foot whose external walls do not become heated, thereby eliminating the possibility of burning some part of the patient's body.

DESCRIPTION OF THE PREFERRED EMBODIMENT

An apparatus for treating athlete's foot according to this invention comprises an inner box placed in an outer box. A space is left between the internal walls of the outer box and the external walls of the inner box. The interior of the inner box serves as an aerosol chamber. A heat source is provided in the lower part of the aerosol chamber, and an aerosol generating plate is placed thereon. An ultrasonic wave oscillator, directed to the inside of the aerosol chamber, is attached to the ceiling thereof. An exhaust port communicating with the interior of the outer box is provided in the upper part of the aerosol chamber. An exhaust filter and fan are provided in the upper part of the outer box. A common opening to insert the affected part is provided in one side of both outer and inner boxes, and the common opening is closed with a sealing member.

Figure 1:
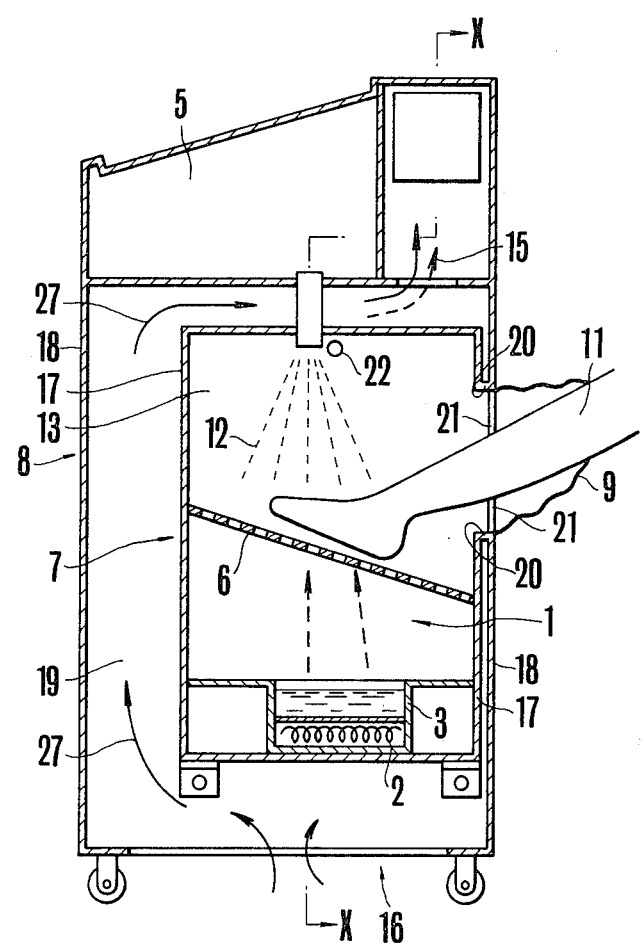
FIG. 1 is cross-sectional view of an apparatus for treating athlete's foot according to this invention.
Figure 2:
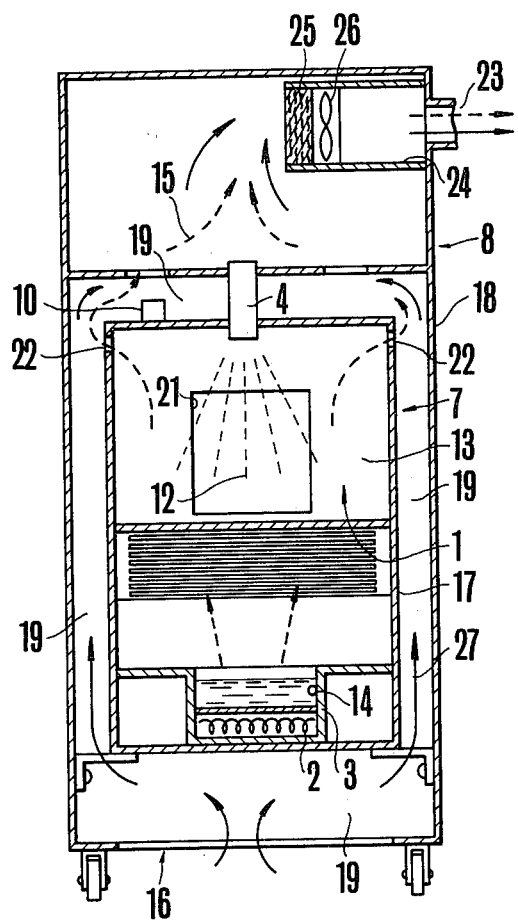
FIG. 2 is a cross-sectional view of FIG. 1, taken along the line X—X.

As shown in FIGS. 1 and 2, an inner box 7 is disposed in an outer box 8, with a space 19 left between the walls 18 of the outer box 8 and the walls 17 of the inner box 7. Windows 21 communicating with the outside are provided in one of the walls 17 of the inner box 7 and one of the walls 18 of the outer box 8, and the windows 21 of the inner box 7 and outer box 8 are connected by a short passage 20. Accordingly, the space 19 between the walls 18 of the outer box 8 and walls 17 of the inner box 7 is smaller on that side where the windows 21 are provided, when compared with the other sides.

The windows 21 are closed with a sealing member 9 which is adapted to closely fit around the hand or foot of a patient, preventing the leakage of the heat and aerosol to the outside.

An exhaust port 22 communicating with the space 19 is provided in the upper part of the side wall 17 of the inner box 7. A pipe 24 leading to the exhaust port is provided in the upper part of the outer box. The pipe 24 contains a layer of adsorbent 25 at one end thereof and an exhaust fan 26 in the middle thereof.

The air in the outer box 8 is sucked up by the exhaust fan 26, and then discharged through an exhaust port 23. Meanwhile, fresh cold air, introduced through an inlet 16 at the bottom of the outer box 8, rises through the space 19 between the outer and inner boxes, then further upward carrying an aerosol 13 flowing out of an aerosol chamber 1 through the exhaust port 22, and eventually flows outside through the exhaust port 23 via the adsorbent layer 25. With the aerosol particles adsorbed by the adsorbent layer 25 comprising activated charcoal and the like, only air is discharged through the exhaust port 23, leaking no offensive smell at all. Furthermore, the constant flow of cold air between the inner and outer boxes prevents the transfer of heat from the inner box to the outer box, thereby eliminating the possibility of burning a hand, etc., by touching the outer box. Wheels are provided under the outer box to facilitate the movement of the apparatus.

Reference numeral 1 designates an aeroso chamber. A heat source 2, such as an electric heater, is provided in the bottom thereof, and an oil plate 3 is placed on the heat source 2. The oil plate 3 is equipped with a thermostat, so that the heat source 2 is shut off when the oil temperature reaches a predetermined level. The oil plate contains a vegetable oil consisting mainly of glycerides of linolic, oleic, palmitic, stearic, arachdinic and other acids, which, when heated by the electric heater, generates an aerosol 13.

Figure 3:
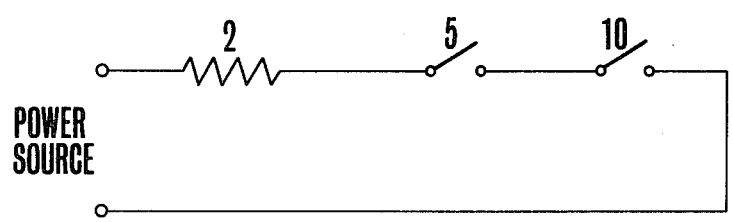
FIG. 3 is a schematic diagram of the apparatus according to the present invention.

A lattice 6 is mounted above the oil plate 3 so that the patient can place the affected hand or foot thereon without touching the aerosol generating source. An ultrasonic-wave generator 4 on the ceiling of the aerosol chamber 1 generates sound waves 12 that concentrate the aerosol to the affected part, increasing the curing effect thereof. A temperature control 5 maintains the temperature within the aerosol chamber 1 at a desired level. Namely, the heat source 2 is turned on and off by the electrically connected temperature control 5. The temperature control 5 is interlocked with an electrically connected temperature sensing unit 10 which is disposed inside the aerosol chamber 1. (See FIG. 3) More specifically, the temperature control 5 controls the chamber temperature to the desired level by means of the temperature sensing unit 10 in the aerosol chamber 1 which is connected to the heat source 2 heating the oil plate 3. The combination of the temperature control 5 and temperature sensing unit 10 in the aerosol chamber 1 automatically controls the heat source 2 so that the temperature in the aerosol chamber 1 does not become so high as to cause a burn. The heat source 2 serves a double function; to raise the temperature in the aerosol chamber 1 and to heat and oxidize the oil in the oil plate 3 to form the aerosol. This function can be performed by controlling the chamber temperature to a predetermined level. Once heated to a high temperature (120° C. to 180° C.), the oil continues to oxidize thereafter even at a somewhat lower temperature (100° C.). In the presence of a catalyst, the oxidization proceeds even at 50° C. As a result of such chamber temperature control and continual oil oxidation, the affected part is protected from burning that might result from overheating.

First, electricity is supplied to the heat source 2, which, then heat the aerosol generating material in the plate to generate the aerosol. When the liquid temperature in the plate reaches the predetermined level, the heat source automatically becomes de-electrified. The automatic control regulates the heat source so that the chamber temperature does not exceed the predetermined level. Next, the fan 26 is started, either manually or by an auxiliary contact of heat control 5. When an adequate amount of aerosol has been generated, the affected hand or foot 11 is inserted through the window 21 into the aerosol chamber 1, with the sealing member 9 fitting closely around the hand or foot to prevent the leakage of the aerosol. Then, ultrasonic waves are generated. The treatment time is controlled either manually or by use of a timer. When the hand or foot is thus kept inside the aerosol chamber 1 for several ten minutes, the aerosol contacts and reacts with the fungus, producing the curing effect. By turning on the fan 26 during the treatment, the aerosol form the erosol chamber is adsorbed by the activated charcoal, emitting no offensive smell outside. Furthermore, the outer box does not become substantially hotter than room temperature.

As described above, the apparatus according to this invention can treat athlete's foot without emitting an offensive small and without creating the danger of burning due to contact with a highly heater outer box.

What is claimed is:

1. An apparatus for treating athletes's foot which comprises:
    an outer box having an air intake port therein;
    an inner box placed within said outer box such that there is a space between the walls of said outer box and the walls of said inner box, the inner box forming an aerosol chamber;
    a heat source located in a lower portion of said aerosol chamber;
    an aerosol generating plate located on top of said heat source;
    an ultrasonic wave oscillator located within said chamber and affixed to a wall thereof, said oscillator being directed toward the interior of said aerosol chamber;
    an exhaust port provided in an upper portion of said aerosol chamber so as to communicate with said outer box;
    an exhaust filter and fan provided in an upper portion of said outer box and located adjacent to an outer exhaust port provided in one of the walls of said outer box so as to communicate with the atmosphere outside of said outer box, said fan causing a flow of air from said air intake port through said space between said outer box and said inner box through said exhaust filter and from said exhaust port through said exhaust filter to said atmosphere through said outer exhaust port;
    an inserting port communicating with the aerosol chamber, said port being in common with one wall of both said outer and inner boxes;
    and flexible sealing means for sealing said inserting port about a leg of a user.

* * * * *